United States Patent [19]
Wenke et al.

[11] Patent Number: 5,628,799
[45] Date of Patent: May 13, 1997

[54] **HAIR DYING METHODS AND KITS WHICH CONTAIN A *DOPA* SPECIES, REACTIVE DIRECT DYE, AND A FERRICYANIDE OXIDANT**

[75] Inventors: Gottfried Wenke, Woodbridge, Conn.; Giuseppe Prota, Naples, Italy

[73] Assignee: Clairol Incorporated, Stamford, Conn.

[21] Appl. No.: 484,041

[22] Filed: Jun. 7, 1995

Related U.S. Application Data

[63] Continuation of Ser. No. 159,988, Nov. 30, 1993, abandoned, which is a continuation-in-part of Ser. No. 766,606, Sep. 26, 1991, Pat. No. 5,273,550, Ser. No. 909,371, Jul. 13, 1992, Pat. No. 5,279,617, and Ser. No. 923,078, Jul. 31, 1992, Pat. No. 5,279,618.

[51] Int. Cl.⁶ ......................................... A61K 7/13
[52] U.S. Cl. ..................... 8/407; 8/408; 8/410; 8/414; 8/415; 8/424; 8/623; 8/624; 8/629
[58] Field of Search ............................. 8/405, 406, 407, 8/408, 409, 410, 411, 412, 414, 415, 424, 623, 624, 629

[56] References Cited

U.S. PATENT DOCUMENTS

| | | | |
|---|---|---|---|
| 2,875,769 | 3/1959 | Rosmarin et al. | 132/7 |
| 3,698,852 | 10/1972 | Pantzer et al. | 8/10.2 |
| 3,907,494 | 9/1975 | Saygin | 8/408 |
| 3,993,436 | 11/1976 | Fujinuma | 8/10.2 |
| 4,453,941 | 6/1984 | Jacobs | 8/424 |
| 4,473,374 | 9/1984 | Bugaut et al. | 8/421 |
| 4,746,322 | 5/1988 | Herlihy | 8/405 |
| 4,776,857 | 10/1988 | Carroll et al. | 8/405 |
| 4,904,274 | 2/1990 | Schultz et al. | 8/406 |
| 4,961,925 | 10/1990 | Tsujino et al. | 8/406 |
| 5,011,500 | 4/1991 | Grollier et al. | 8/423 |

*Primary Examiner*—Paul Lieberman
*Assistant Examiner*—Caroline L. Dusheck
*Attorney, Agent, or Firm*—Charles J. Zeller

[57] ABSTRACT

A process for dyeing hair by preparing and applying to the hair an aqueous reaction medium comprising a dopa species, a reactive direct dye and an oxidant, said aqueous reaction medium optionally containing at least one hair dyeing agent selected from the group consisting of primary intermediates and couplers and also containing a buffer to maintain the pH in the range from 6 to 10 during the reaction, and removing said aqueous reaction medium from the hair within about one hour following its preparation.

25 Claims, No Drawings

HAIR DYING METHODS AND KITS WHICH CONTAIN A *DOPA* SPECIES, REACTIVE DIRECT DYE, AND A FERRICYANIDE OXIDANT

RELATED APPLICATIONS

This application is a continuation of commonly owned patent application Ser. No. 08/159,988 filed Nov. 30, 1993, now abandoned, which is a continuation-in-part of commonly owned patent application Ser. Nos. 07/766,606; 07/909,371 and 07/923,078 filed Sep. 26, 1991; Jul. 13, 1992 and Jul. 31, 1992 respectively, now U.S. Pat. Nos. 5,273,550; 5,279,617 and 5,279,618 respectively.

FIELD OF THE INVENTION

The present invention relates to the use of dopa (dihydroxyphenylalanine) and/or a substituted dopa (together "dopa species") compound to generate melanin pigments to dye hair permanently. More specifically, the present invention relates to a hair dyeing process wherein the dopa species and an oxidant react in an aqueous environment to provide unexpectedly high concentrations of a nitrogenous phenolic, especially indolic, melanin precursor in the aqueous environment, the melanin precursor formed during the reaction being effective to dye hair permanently upon its coincident conversion to melanin while in the hair. The present invention further relates to the formation of such melanin precursors by reaction(s) with the dopa species, the oxidant and one or more hair dye compounds selected from direct dyes, primary intermediates and couplers. In addition, the present invention concerns a method of dyeing hair wherein the melanin is generated by the user from separately packaged reactants sold in the form of a kit.

BACKGROUND OF THE INVENTION

As reported, for example, in Prota, *Progress in the Chemistry of Melanins and Related Metabolites*, Med. Res. Reviews, 8:525-56 (1988), melanins are naturally occurring pigments present in hair and skin. In humans, biosynthesis takes place in tyrosinase containing melanocytes. The tyrosinase enzyme catalyzes the hydroxylation of tyrosine to dopa and its subsequent oxidation to dopachrome. Once formed, dopachrome undergoes a series of complex reactions in the formation of eumelanins and phaeomelanins.

Melanins provide black and deep brown pigments, and are formed by oxidative polymerization of 5,6-dihydroxyindole derived biogenetically during the melanogenesis. On the other hand, phaeomelanins provide yellow to reddish brown pigmentation to hair and are formed by oxidative polymerization of cystein-S-yl-dopas via 1,4-benzothiazine intermediates.

Synthetic 5,6-dihydroxyindole (DHI) has been disclosed in the prior art for use in hair and skin dyeing. For example, U.S. Pat. No. 2,934,396 to Charle discloses a process for dyeing hair by contacting hair with an aqueous solution of DHI having a pH of at most 7 for 5 to 60 minutes, followed by an application of an aqueous solution capable of inducing oxidation and/or polymerization of DHI.

Dopa and dopamine are disclosed as hair dyeing precursors in the process of Herlihy, U.S. Pat. No. 4,746,322, wherein the aqueous hair dyeing composition comprises said precursor, an organic compound to assist dye dispersion and an iodate or periodate. The dopa or dopamine dye precursor is present in the aqueous hair dye composition in an amount of from about 1 to about 100 mg/ml, preferably from about 5 to about 25 mg/ml. Dopamine is preferred, according to Herlihy. The iodate or periodate is present in the composition at a concentration of 1 to about 50 mg/ml, while the dispersing agent is present in an amount of from about 0.1 to 30% (wt./vol.). Optionally, a color modifier can be incorporated into the aqueous composition of Herlihy, at a level of from about 0.1 to about 10 mg/ml. pH may be maintained between about 3 to about 7 by incorporation of an effective amount of a buffer. According to Herlihy, the above-described aqueous compositions disperse the dye on the hair shaft "with little or no penetration into the hair shaft." Column 2, lines 56–58.

The prior art fails to provide a commercially feasible process for effectively, permanently dyeing hair using dopa as a starting reagent. It is believed this failing is attributable to an inability of the prior art processes in making a melanin precursor available on the hair at concentrations suitable for its diffusion into the hair, for subsequent conversion to nondiffusable melanin, as further explained in detail below.

Indeed, the inability to provide an inexpensive yet effective process for dyeing hair with a melanin precursor has prevented use of melanogenesis in the commercial dyeing of hair.

Interest in melanogenesis to dye hair is quite high, however. This is because synthetic melanin pigments provide an exceptionally natural-looking deep brown or black color. Moreover, they are not irritating to the skin. Nor are they mutagenic.

It has now been found, quite surprisingly, that an aqueous hair dyeing process wherein an effective melanin-forming hair dyeing amount of 5,6-dihydroxyindole is generated during the reaction of dopa with an oxidant can be practiced inexpensively and under commercially feasible conditions, to achieve a permanent hair color.

It has also been found that an aqueous hair dyeing process, wherein an effective melanin-forming hair dyeing amount of a nitrogenous phenolic, especially indolic, melanin precursor is generated during the reaction of select substituted dopa compounds with an oxidant, can be practiced inexpensively and under commercially feasible conditions, to achieve a permanent hair color. Advantageously, the utilization of the substituted dopa compounds of the present invention is conducive to the attainment of a range of hair color shades, in contrast to the use of dopa alone as the starting reagent, which is capable merely of providing gray or black pigmentation to hair.

It has additionally been found that even further and more desirable color modifications to hair dyed in accordance with the process of the present invention may be obtained by including in the reaction mixture, along with the dopa and/or substituted dopa compound, one or more hair dye compounds selected from the group consisting of direct dyes, primary intermediates and couplers.

The hair dyeing process of the present invention contemplates the preparation of an aqueous hair dyeing composition by reacting dopa or a selected substituted dopa compound as hereinafter defined, with a ferricyanide oxidant to form a melanin-forming hair dye precursor, and applying the aqueous composition to the hair. The melanin precursor contained in said aqueous composition is capable of diffusing into the hair shaft in an amount effective to dye hair permanently upon its coincident conversion to melanin while in the hair.

The aqueous hair dyeing composition is produced by initiating reaction between the dopa species or a salt thereof with an inorganic oxidant that is a soluble ammonium, alkali or alkaline earth metal salt, especially sodium and potassium salts, of ferricyanide in an aqueous reaction medium buffered by sufficient buffering agent to maintain the reaction medium pH from about 6 to about 10 throughout the series of reactions that take place leading to the melanin precursor.

In order to achieve the permanent dyeing of hair in accordance with the process of the present invention, it is critical to generate melanin from the melanin-forming hair dye precursor in the aqueous hair dye composition in such amount as to effect a color change to the hair. The total color change may be gradually obtained by several applications of the composition over time, or may be effected by a one-time application of the composition, depending on the concentration of the dopa species, the duration of application, and the desires of the user. It is further critical that the hair dye composition be applied to the hair prior to the substantial formation of melanin so that the melanin precursor formed during the reaction may diffuse into the hair prior to the generation of melanin, the melanin then being formed within the hair. It is additionally important that the process for dyeing hair as described herein be capable of completion within less than about one hour.

In the case in which the dopa species is dopa or a salt thereof, the reaction with the oxidant leads to the formation of 5,6-dihydroxyindole, which melanin precursor, upon its conversion to melanin, provides hair with a permanent black color. In the case of the selected substituted dopa compounds, melanin precursors are obtained which, upon conversion to melanin, produce a range of shades depending upon the selection of the substituted dopa compound.

A further aspect of the invention is the optional incorporation of an hair dye component selected from the group consisting of direct dyes, primary intermediates, couplers and mixtures thereof in the reaction mixture. Following the initial dopa species-oxidant reaction, it is believed that the direct dyes, primary intermediate(s) and/or coupler(s) present in the reaction mixture react at least in part with the intermediate compounds formed prior to the melanin precursor, thereby providing chromatic characteristics to the melanins ultimately obtained.

In another aspect of the present invention, it has been found that the formation of indolic melanin precursors such as 5,6-dihydroxyindole is hastened by proper selection and amount of the buffer, apart from its requirement for maintaining pH of the reaction medium. Preferably, the buffer is a phosphate, carbonate or bicarbonate, and typically is included in substantial excess over the amount needed to maintain the requisite pH.

In yet another aspect of the present invention, the process for dyeing hair contemplates treatment of the hair with agent(s) that promote melanin formation, e.g., a solution of a metal ion salt, which treatment accelerates the formation of melanin from the ultimate indolic precursor. Treatment with the promoting agent may be a pre- or a post-treatment, or in some instances may be conducted simultaneously with the application of the hair dye composition of the present invention.

The process of the present invention may conveniently be practiced by providing premeasured amounts of the reactants in separate containers packaged in kit form. The user simply admixes the reactants on or with subsequent application to the hair and allows the composition while it is reacting to remain on the hair for the prescribed period of time. It is seen that no special expertise is required to carry out the process, and accordingly the product and process are equally suitable for in-home use by the nonprofessional as well as salon use by the professional. Advantageously, the product in kit form is shelf-stable and is therefore suitable for retail sale and without precautions generally required for melanin-forming precursors, such as 5,6-dihydroxyindole, e.g., storage under anaerobic conditions.

DETAILED DESCRIPTION OF THE INVENTION

The hair dyeing process of the present invention comprises the preparation of an aqueous hair dyeing composition by reacting dopa or selected substituted dopa or dopa analogs (hereinafter referred to collectively as the "dopa species"), and an inorganic oxidant, in the presence of a direct dye and, optionally, in the presence of another oxidative hair dye component selected from the group consisting of primary intermediates, couplers, and mixtures thereof and contacting the hair with said hair dyeing composition for a period of time of about less than one hour, said reaction proceeding in such manner and under such conditions as to provide on the hair an amount of a melanin-forming hair dye precursor during the period of contact effective to generate a hair dyeing amount of melanin. The precursor diffuses into the hair during the period of contact and forms melanin in situ in the hair to provide a permanent color. Preferably, the contact time of the hair dyeing composition on the hair is from about 5 to about 45 minutes, most preferably from about 5 to about 30 minutes.

By "permanent" is meant a color not removable by shampooing with a conventional surfactant-containing shampoo, the permanency being attributable to the inability of melanin to diffuse from the hair shaft in view of its molecular size.

By "melanin" is meant a synthetically derived pigment formed by polymerization of a melanin precursor, i.e., the formation of molecules too large to be removed from the hair.

By "melanin-forming precursor" is meant the reaction product(s) of the dopa species with a ferricyanide oxidant and optionally with a direcy dyes primary intermediate or coupler hair dye component, which reaction product(s) undergoes polymerization to form melanin. Such melanin precursors generically are nitrogenous phenolic compounds and are indolic compounds, except to the extent that cyclization to form the indole ring might be prevented in view of reactions occurring with direct dyes and, optionally, with couplers and/or primary intermediates, as hereinafter disclosed.

Applicants herein believe that the terms "melanin" and "melanin precursor" as used herein with respect to the reaction products of the selected dopa species of this invention are terms which are will understood by one or ordinary skill in the field, even though the chemical identity of the melanin precursors, particularly those precursors formed by reaction with direct dyes or, if present, with primary intermediates and/or couplers, and especially the melanins formed in accordance with the process of the present invention, may not be precisely known or understood.

In another aspect of the present invention, the dopa species and the oxidant reactant is separately provided in kit form, for admixture by the user to initiate the reaction. It is possible to combine the reactants directly on the hair of the user, but preferable to mix them in a mixing vessel, for subsequent application to hair following commencement of the reaction.

It has been found that the color obtained by oxidation of the dopa species can be significantly modified by including direct dyes and, if desired, primary intermediates and/or couplers in the reaction medium. In this regard, the terms "melanin precursor" and "melanin" are intended to include reaction products of direct dyes, primary intermediates and couplers with the dopa species and with reaction products of the dopa species produced by oxidation with the oxidant. While such melanin precursors are nitrogenous phenolic compounds, it is not known whether they have an indole ring in their chemical structure.

The hair dyeing process involves a series of reactions leading to the formation of one or more melanin precursors capable of diffusing into the hair shaft. Within the hair shaft, the precursor is oxidized by air to melanin, which is incapable of diffusion out of the hair shaft. Accordingly, the melanin precursor-containing hair dye composition must be applied to the hair prior to the substantial formation of melanin. Inasmuch as the precursor, upon formation, will begin its conversion to melanin by reaction with air, it is critical to apply the reaction medium to hair prior to onset of substantial melanin formation, that is, at or shortly after admixture of the reactants.

The term "applying" as used herein means the contact between the hair dye composition and the hair as described above. Placing the hair dye composition on the hair following substantial melanin formation is not operable since the insoluble melanin will not diffuse into the hair, and will be largely stripped away during subsequent shampooing. For convenience, a contact time of "less than about one hour" as used throughout this application is measured from the onset of mixing of the reactants.

In the process of the present invention, the dopa species is oxidized by the oxidant through a series of reactions leading to the formation of one or more melanin precursors. While not wishing to be bound by any particular reaction scheme, applicants herein believe that the following reactions occur leading to the formation of the melanin precursors: (1) oxidation of the dopa species by the ferricyanide oxidant followed by cyclization, further oxidation and rearrangement with carbon dioxide release, leading to the formation of an indole, e.g., the conversion of dopa to 5,6-dihydroxyindole, (2) oxidation of the dopa species followed by cyclization, further oxidation and rearrangement without carbon dioxide release, and (3) reactions wherein the initial dopa species oxidation product(s) is modified by further reaction with a direct dye or with with a coupler or primary intermediate when these are present, leading to nonindolic nitrogeneous phenolic compounds.

In the case of dopa, for example, dopa is oxidized to dopaquinone, which spontaneously forms cyclodopa. Additional oxidant further reacts with the cyclodopa to form dopachrome which undergoes spontaneous, although not immediate, transformation to 5,6-dihydroxyindole through rearrangement of the dopachrome species and the release of carbon dioxide. Analogous reactions also take place with regard to alpha alkyl dopas. Dopa alkyl esters also react similarly, but without release of carbon dioxide. The reactions for the preparation of melanin from dopa in accordance with the present invention are presented below.

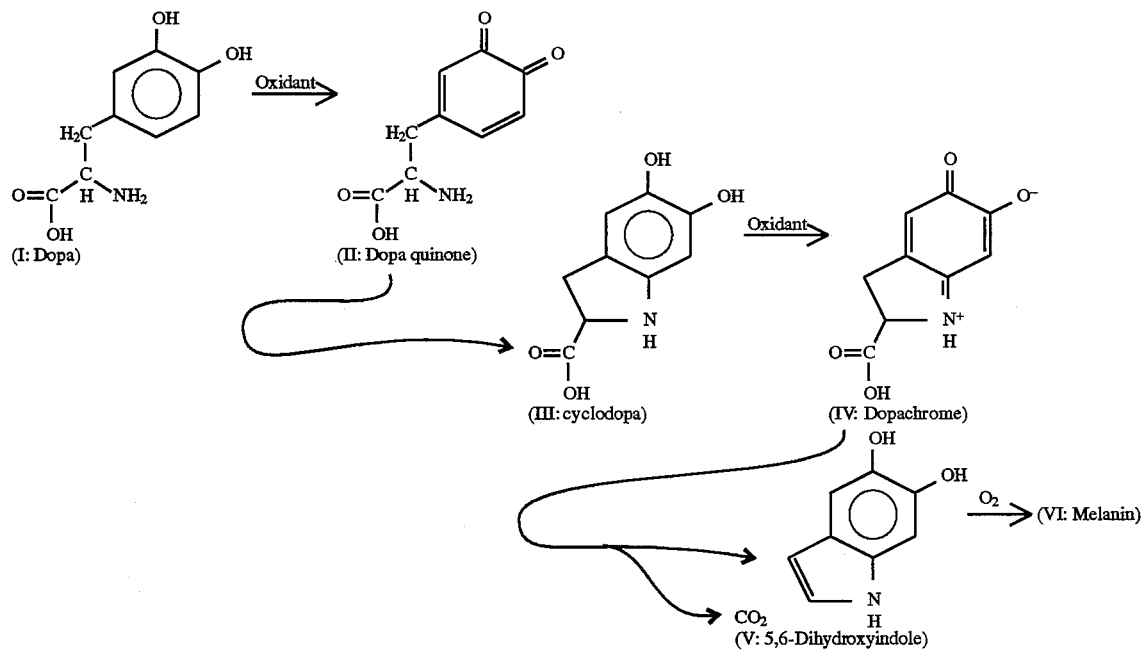

It should also be understood that a suitable aqueous hair dyeing composition can be obtained without adding additional constituents to the aqueous reaction medium. That is, the aqueous reaction medium and the aqueous hair dyeing composition may be regarded as equivalents, for example, in the case where the reactions involved occur, in whole or in part, upon the hair to be dyed. As described below, however, it is preferred to include additional optional constituents, e.g., thickeners, etc., to provide a more elegant product.

It is seen that the sequence of reactions contemplated in the process of the present invention is conducive to many possible competing reactions. Because second order reactions are likely to be involved, the problem of unwanted competition reactions becomes especially acute when the concentrations of starting reactants in solution are high, as in the process of the present invention.

A second difficulty believed to exist is that the rearrangement of cyclized indolic compounds, when it occurs, for example, in the conversion of dopachrome to 5,6-dihydroxyindole, is the rate-determining step in the reaction leading to the melanin precursor.

Yet another problem that mitigates against the commercial use of the dopa species as a starting reagent in the dyeing of hair is that the melanin precursor, which oxidizes relatively slowly in air to form melanin, is essentially immediately oxidized by unreacted oxidant to form by-products unsuitable for permanently dyeing hair.

In overcoming each of these difficulties, the present invention achieves a melanin precursor concentration in the aqueous hair dyeing composition that leads to a melanin level effective for permanently dyeing hair, and provides a process that can be practiced by the user in under about 60, preferably under 45, most preferably under 30 minutes.

Thus, the present invention contemplates conversion of the dopa species to the melanin precursor at yields and in amounts effective to color hair permanently. To this end, applicants have found that the ferricyanide oxidant, when present in the reaction media in monitored amount, is conducive to the attainment of melanin precursor concentrations in the dyeing composition effective to dye hair.

Accordingly, in the process of the present invention, the amount of oxidant present in the reaction medium relative to the dopa species should be such that the oxidant is largely reacted prior to the appreciable formation of the melanin precursor.

With regard to the second difficulty, it is believed that the above-mentioned rearrangement step may be accelerated by use of particular buffer constituents in a rate-potentiating concentration, thereby permitting completion of the process within about one hour.

The Dopa Species

As previously indicated, the preparation of the aqueous hair dye composition is by the consumer, who admixes the reactants at the time of use. The dopa species or a suitable salt thereof is present in the initial reaction medium at a level suitable to obtain a hair dyeing amount of melanin, which melanin amount, in turn, is dependent on the melanin intermediate levels achieved during the period of contact of the hair dyeing composition with the hair.

The required initial dopa species concentration in the reaction medium may be higher than its solubility limit in water. Accordingly, an acid or alkaline aqueous premix can be prepared prior to preparation of the aqueous reaction medium. Alternatively, the more soluble acid or basic salts can be used in the preparation of the aqueous medium. Use of the salts or the use of an acid or alkaline premix allows the otherwise relatively insoluble dopa reactant to go into solution and be available for rapid reaction.

Illustrative of the suitable soluble acid salts of the dopa species are the hydrochloride and sulfate. The hydrochloride salts are preferred. Among the suitable basic salts that can be used are the soluble alkali metal salts and the alkaline earth metal salts. The sodium and potassium salts are preferred. Any inorganic or organic acid or base can be used to adjust the pH of the dopa species premix solution, provided that the agent used does not interfere in the reactions. Suitable bases are ammonium and sodium hydroxide and mono-, di- and trialkanolamines, especially ethanolamines. Such acids are hydrochloric, phosphoric, tartaric, citric and lactic acids and their salts. Sodium hydroxide and hydrochloric acid are preferred.

The dopa species (or dopa species salt) concentration in the initial reaction medium is from about 2 mg/ml up to about the solubility limit of the dopa species in the reaction medium. Preferably, its concentration is from about 5 to about 25 mg/ml in the initial reaction medium, most preferably from about 5 to about 15 mg/ml.

The dopa species is selected from dopa and substituted or analog dopa compounds. Substituted or analog dopa species (referred to herein as the "substituted dopa" species) suitable in the process of the present invention are alpha alkyl dopa having 1 to 4, preferably 1 to 2, carbon atoms in the alkyl groups, epinephrine (adrenaline) and dopa alkyl esters having 1 to 6, preferably 1 to 2, carbon atoms in the alkyl group.

Alpha alkyl dopa is oxidized by the ferricyanide oxidant in analogous manner to dopa, to form 5,6-dihydroxy-2-alkylindole, which forms melanin by aerobic oxidation.

Epinephrine, which has the structure:

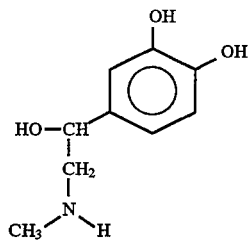

reacts with the ferricyanide oxidant to form adrenochrome. It is believed that adrenochrome rearranges to form adrenolutin and various indolic and/or isatinic derivatives.

In the case of the dopa alkyl esters, oxidation proceeds to form the corresponding esters of 5,6-dihydroxyindole-2-carboxylic acid, which reaction proceeds without decarboxylation, i.e., there is no release of carbon dioxide. This ester of 5,6-dihydroxyindole-2-carboxylic acid then polymerizes to melanin by aerobic oxidation.

The Oxidant Component

Suitable as the oxidant for use in the present invention is a soluble ammonium, alkali metal and alkaline earth metal salt, especially ammonium, sodium and potassium salt of ferricyanide. Advantageously, the reduced form of ferricyanide—ferrocyanide—present in the aqueous solution following the reaction will not further react with the melanin precursor in the aqueous system, thereby maximizing the formation of the melanin precursor and hence increasing the overall efficiency of the process.

The oxidant is quite reactive towards the dopa species present in the reaction medium during the process. Thus, the initial reaction between the dopa species and the oxidant goes essentially to completion within less than five minutes, most likely in less than one minute, and might even be regarded as instantaneous in some instances. For this reason, intermediates in the postulated reaction schemes leading to the formation of the melanin precursor are short-lived in the reaction media and not available for inter-reaction. Accordingly, in the process of the present invention, unwanted side reactions are prevented or greatly limited.

The oxidant reactant is present in the initial reaction medium at a substantially stoichiometric equivalent concentration, as further described below.

During the conversion of the dopa species to the melanin precursor, each dopa species molecule loses four electrons. Accordingly, if an oxidant is employed that gains one electron, such as ferricyanide, four molar equivalents of oxidant are required to convert dopa to dihydroxyindole. Thus, two molar equivalents of ferricyanide are needed to convert dopa to dopaquinone and another two molar equivalents of ferricyanide are required to convert cyclodopa (spontaneously obtained from dopaquinone) to dopachrome.

In the case of dopa, one "stoichiometric equivalent" as used herein is equal to the number of molar equivalents of an oxidant necessary to convert one mole of dopa to one mole of dopachrome (which spontaneously forms dihydroxyindoles). For the substituted dopa species, analogous reactions are believed to occur. Thus, the alkyl dopa species form alkyl dihydroxyindoles, the alkyl dopa esters form dihydroxyindole carboxylic acid esters, and epinephrine is believed to form adrenolutin, each conversion resulting in the loss of four electrons.

A greater than about a stoichiometric equivalent amount of oxidant relative to the dopa species employed is not recommended, as the excess oxidant will react with the melanin precursor. The dopa species (dopa or substituted dopa) in an excess stoichiometric equivalent amount relative to oxidant is preferred to ensure that unreacted oxidant does not remain following the reaction. An excess of the dopa species does not appear to affect the process performance, although unreacted substituted dopa would tend to reduce the overall efficiency of the process. Generally, the stoichiometric equivalent ratio on a molar basis of the dopa species to ferricyanide initially present in the reaction medium will be from about 1.25:1 to 0.95:1, preferably from about 1.1:1 to 1:1, most preferably from about 1.05:1 to 1.01:1.

When the oxidative hair dye components are optionally incorporated in the reaction mixture, it is believed that the direct dye, primary intermediate and/or coupler hair dye compounds react with one or more of the intermediate reaction products prior to rearrangement of the cyclized intermediate. Further, it is believed that a portion of the dopa species initially present in the reaction medium is reacted to completion to form 5,6-dihydroxyindole or the equivalent analog melanin precursor. Theoretically, then, when the optional oxidative hair dye components are incorporated, the initial reaction medium should contain between two to four molar equivalents, i.e., between 0.5 to 1 stoichiometric equivalents of oxidant relative to the dopa species based on complete conversion of dopa to the melanin precursor. Accordingly, the stoichiometric equivalent ratio on a molar basis of the dopa species to oxidant initially present in the reaction medium is generally from about 1:1 to 2:1, preferably from about 1.2:1 to 1.8:1, most preferably from about 1.3:1 to about 1.7:1. The stoichiometric equivalent amount of oxidant relative to dopa should not be so great as to cause an excess of the oxidant to be present after formation of the melanin precursor, because oxidation of the melanin precursor by the oxidant is not desirable.

It might be possible to add oxidant slowly or in stages during the reaction. However, this would be difficult and inconvenient for the consumer, and may inadvertently result in oxidant being present when the melanin precursor is formed.

The Buffering Agent Component

Inasmuch as the pH of the reaction medium will fall during the reactions, it is necessary to provide a sufficient amount of a buffering agent in the reaction medium to maintain the requisite pH. In the process of the present invention, it is critical to maintain the pH of the aqueous reaction medium between about 6 to 10 during the melanin precursor-forming. Preferably, the pH is between about 6 to about 8.5, and especially alkaline to about 8.5.

In addition to controlling reaction medium pH within the aforesaid limits, the buffers employed in the process of the present invention are believed to assist in the formation of the melanin precursors. Thus, it has been observed that as the concentration of the buffers in the reaction medium increases, the rate of the rearrangement of dopachrome and its analog also increases. Thus, the buffers potentiate the rearrangement reaction, thereby decreasing the time for the generation of the melanin precursor, which permits the hair dyeing process to be completed within about one hour from the onset of the dopa species oxidant reaction. Typically, the buffer is present in an amount in excess of that needed to buffer the reaction mixture. Preferably, then, it is desirable to provide 2 to 25 times, especially 5 to 20 times, as much of these particular buffers as would be needed merely to maintain the reaction mixture pH within the prescribed limits.

Buffers found to be suitable for use in this invention are ammonium and alkali metal phosphates, bicarbonates, carbonates and, to a lesser extent, borates. Also suitable are aminic buffers such as N-[2-hydroxyethyl]piperazine-N'-[2-ethanesulfonic acid] (HEPES), N-[2-acetamido]-2-aminoethane sulfonic acid (ACES), tris[hydroxymethyl] aminomethane (TRIZMA) and N-trist[hydroxymethyl]-methyl-3-aminopropane sulfonic acid (TAPS). The ammonium and alkali metal carbonates and bicarbonates are suitable, even though not typically employed in the stated pH range. The preferred buffers used in the practice of the present invention are sodium and potassium carbonate, bicarbonate or phosphate when the oxidant is ferricyanide and phosphate buffer with the permanganate oxidant. Other buffers suitable for maintaining reaction medium pH and to potentiate the rearrangement reaction may exist which may be determined by simple experimentation, as herein disclosed in the examples.

The Process Parameters

It should be understood that the ability to obtain the necessary melanin precursor concentration depends on both its yield and the amount of the dopa species available for conversion. Thus, a lower melanin precursor yield would be acceptable when a high initial dopa species concentration is provided in the reaction medium. Conversely, a relatively high melanin precursor yield would be needed if a low dopa species concentration is used.

In the present invention for permanently dyeing hair, the melanin precursor is converted to melanin in situ while the hair dyeing composition is in contact with the hair. Thus, the process should be viewed as a dynamic one in which the various reactions leading to melanin proceed simultaneously. Accordingly, the concentration and molar yield of the melanin precursor based on the dopa species formed in the hair dye composition is not directly measurable unless the subsequent melanin-forming reaction is prevented. Even then, the measurement of the yield is complex in view of the number of competing reactions and the number of chemical species present. The measurement are especially complex and difficult for the substituted dopa species, in particular, epinephrine, and when the reaction mixture further includes a direct dye, coupler or primary intermediate. Similarly, amount and yield of melanin is not easily quantitatively measurable because it is formed in the hair. On the other hand, the effectiveness of the process may be determined by measuring the change in hair color when a hair swatch is treated in accordance with the process. Further, such evaluation is an indication of the amount of melanin that has formed in the hair shaft, and hence the amount of precursor that has diffused into the hair shaft during the treatment. The test procedure is discussed further below. As a guide to the successful practice of the invention, applicants have found that a perceptible color change to hair occurs within one hour of application to the hair. A suitable melanin precursor molar yield is typically obtained when the initial dopa species concentration is from about 2 mg/ml up to its solubility limit in the reaction medium.

In the case where dopa alone is contained in the reaction medium (i.e., other direct dyes, couplers and/or primary intermediates are not present), applicants have found that a perceptible color change to hair occurs within one hour of application to the hair when a peak 5,6-dihydroxyindole (DHI) concentration obtained in the hair dyeing composition is at least about 1.5 mg/ml. This peak DHI concentration, which may be regarded as a practical minimum, occurs typically during the early stage of the reactions described above, normally within the first 30 minutes, preferably within the first 20 minutes, of reactant admixture. An initial dopa concentration of about 3 mg/ml, coupled with DHI molar yield of about 65%, is suitable to achieve the practical minimum peak DHI level in the aqueous composition. It should be understood that the peak DHI concentration is measured during the reactions occurring in the reaction medium and in isolation from the hair, as set forth, for example, in Examples 1–11. As measured by HPLC, molar yields of DHI in accordance with the present invention are typically from about 50 to about 70%, with molar yields of the by-product dihydroxyindole carboxylic acid being from about 7 to 9%, both yields being based on conversion of dopa. Preferably, the peak DHI concentration obtained in the aqueous composition is above about 2.5 mg/ml, most preferably above about 4 mg/ml. DHI molar yields above about 50% and initial dopa concentrations from about 5 mg/ml to the solubility limit in the reaction medium of the dopa species employed are preferred to establish levels of DHI in the hair dye composition suitable to generate a hair dyeing amount of melanin. Of course, the incorporation of the direct dye, primary intermediate and/or coupler hair dye components in the reaction medium will decrease the amount of the 5,6-dihydroxyindole melanin precursor obtained, in favor of other melanin precursors that are not easily quantifiably measured.

For the substituted dopa compounds, a suitable melanin precursor molar yield is typically obtained when the initial substituted dopa concentration is from about 2 mg/ml up to its solubility limit in the reaction medium. Thus, from in vitro experiments it has been found that an initial concentration of alpha methyl dopa of 2 mg/ml yields about 1.5 mg/ml methylindole, which corresponded to about a 90% molar yield. When the initial alpha-methyl dopa concentration was about 8–9 mg/ml, the molar yield was about 60–65%. Similarly, an initial dopamethylester concentration of 2 mg/ml was found to provide dihydroxyindole-2-carboxylic acid methyl ester at about 95% molar yield.

Systems wherein the melanin precursor molar yield and the initial dopa concentration cooperatively provide high melanin precursor concentrations are especially suitable to effect a color change in one treatment in accordance with the present invention, while systems that provide lower melanin precursor concentrations are particularly useful to color hair gradually over successive treatments in accordance with the disclosed process. Typically, 2 to 14 successive treatments for shorter time periods (each less than about 10 minutes, especially less than 5 minutes) are used to color hair gradually.

In the practice of the present invention, the user is provided with two or more containers of reactant-containing solutions, and with printed instructions to mix the solutions in order to form the hair dye composition and to apply the dye composition to the hair for a period of less than about one hour. The process is generally conducted at room temperature, although elevated temperatures obtained by means of a hair dryer, especially in a hair salon, may be used. The user may also place a cap over the hair following the application of the dye composition to the hair, body heat being retained within the cap. Following completion of the contact step, the hair is shampooed to remove excess composition including surface melanin from the hair.

The Hair Dyeing Kit Product

The kit provided in accordance with this aspect of the invention comprises a sufficient amount of buffer, a first container containing a dopa species solution containing the direct dye or, optionally, the primary intermediate and/or coupler, and a second container containing the oxidant solution. The buffer may be individually packaged in a third container, may be present in the first container, or may be present in the second container. The direct dye, and/or coupler primary intermediate may also be in one or more separate containers.

When the dopa species solution is provided in the form of its acid or basic salt, or is acidic or basic in pH, the buffer would not be present therein. While the kit may contain packets containing amounts, preferably premeasured, of dry powders for preparation of these solutions, it is more convenient to provide them as solutions. Moreover, solutions containing premeasured quantities of the constituents facilitates their correct use by the consumer.

One or more additional containers may be provided in the kit, as described below with regard to optional constituents. The optional constituents may also be contained within the solutions, barring any incompatibility.

The consumer admixes the components of the kit, suitably as the aqueous solutions or as dry powders and water, according to written instructions, to obtain the aqueous reaction mixture. The admixture may be conducted in a separate vessel supplied with or external to the kit, or may take place in a container of the kit adapted to provide sufficient head space for mixing. The reactants may also be admixed on the hair of the user. Essentially upon mixing, reaction of the dopa species will commence. The precursor formed will subsequently oxidize in air to form melanin, visually indicated by the formation of color. The reacting mixture is applied to the hair, the completion of the melanin precursor reaction taking place on the hair, with concurrent diffusion of precursor (and/or partially oxidized precursor) into the hair where the melanin is formed, whereby a permanent hair color is obtained. After the desired hair shade is reached, most preferably within about 30 minutes, the hair dye composition that was applied to the hair is removed, preferably with a conventional shampoo.

Because the hair dye composition is applied to the hair initially or shortly after the reactions commence, the reaction time for melanin formation and the contact time on the hair are essentially the same. The kinetics of melanin formation contemplated by the present invention are such that the reaction should take place within the prescribed contact time constraints previously described. However, failure to remove the hair dyeing composition within the prescribed contact time is not consequential, as no appreciable further hair color change will occur.

Melanin Promoting Agents

The formation of melanin from the melanin precursor may be promoted by application of a melanin promoting agent or agents, as described below.

Thus, certain transition metal and zinc ions, for example, copper, zinc, nickel, cobalt and iron ions, accelerate the conversion of the melanin precursor to melanin. As used herein "transition metal" is deemed to include zinc. Solutions containing a salt or mixture of salts having these ions when applied to hair in conjunction with the application of the dye composition of this invention to hair result in a deepening of the color obtained. The transition metal salt ions effect a color change to the hair more rapidly than when they are not used. Typically, the color change is obtained in less than about 30, preferably less than about 15 minutes. Because the precursor that is formed is used more efficiently, lower melanin precursor concentrations are suitable in obtaining significant color in a single treatment. $Cu^{++}$ salts and, to a lesser extent, $Fe^{++}$ salts are preferred.

The metal salt solution may be applied to the hair for a predetermined period of time, typically for about 1 to about 10 minutes, before or after treatment with the hair dyeing composition. As a general rule, application of the metal ion solution during the contact of the hair with the hair dye composition is not preferred, as the metal ion causes melanin to form outside the hair shaft. However, in some instances such simultaneous application might be useful, especially with a metal ion agent such as zinc which more slowly effects melanin promotion.

Excess metal salt is removed from the surface of the hair by rinsing or shampooing prior to the application of the hair dye composition. It is suitable to incorporate the metal ions into a shampoo formulation for pre- or post-treatment, in which event a water rinse will suffice to remove the excess. The metal ions are believed to penetrate into the hair shaft and thus be available to rapidly accelerate the conversion of diffused precursor to melanin upon subsequent treatment with the hair dye composition described herein. The metal salt solution typically contains from about 0.001 to about 1% of the metal salt or salt mixture.

Also suitable to promote melanin formation is an iodide salt when applied in advance of a hydrogen peroxide post-treatment. The iodide may be provided as a 0.01 to 1% solution of the salt, or may be incorporated directly into the hair dye composition. When used as a solution, it may be applied before, during or after treatment of the hair with the hair dye composition. Thereafter, hydrogen peroxide is applied as a 0.1 to 6%, preferably a 1 to 3%, solution.

It is also within the scope of this invention to apply an effective amount of oxidizing solution to the hair as a post-treatment. Suitable oxidizers are, e.g., nitrite, persulfate, periodate, iodate, permanganate and perborate salts in about a 0.1 to 10%, preferably 1 to 5%, aqueous solution.

For best results the agents should be soluble in the aqueous vehicle used in the treatment, and may further contain other adjuvants, such as thickener, surfactant, and the like, e.g., as noted below for the hair dye composition.

Accordingly, the kit containing the first and second pre-mixes may also contain a separately packaged solution of the promoting agent(s). The use of metal salts to enhance the hair color obtained with 5,6-dihydroxyindole is described in British Patent No. 2,132,642, incorporated herein by reference thereto. The use of iodide/peroxide treatment is described in U.S. Pat. No. 4,804,385, and the use of an oxidizing post-treatment is described in U.S. Pat. No. 3,194,734, both patents being incorporated herein by reference thereto.

Colors

The use of dopa alone as the starting reagent to obtain the melanin precursor 5,6-dihydroxyindole is suitable to produce a melanin that dyes hair black or gray. It is unable to produce chromatic colors. When the substituted dopa compounds are employed, the hair dyeing process of the present invention advantageously dyes hair a range of shades depending upon the selection of the starting substituted dopa species. Thus, colors ranging from light to medium brown to black with red, blue, green and yellow tones are possible, depending on the choice of the starting material and the contact time of the hair dye composition on the hair. Alpha methyl dopa has been found to provide a dark brown color, while medium brown has been obtained with dopa methyl ester, and light brown with epinephrine.

The addition of one or more conventional direct dyes which may be employed together with hair dye couplers or hair dye primary intermediates, to the initial reaction mixture provides a means for introducing chromatic colors to the melanin obtained in the practice of the present invention. Thus, colors ranging from light to medium brown to black with red, blue, green and yellow tones are possible, depending on the choice of the starting materials and the contact time of the hair dye composition on the hair.

The various dopa species suitable for use herein may be used singly or in admixture, alone or in combination with one or more of the oxidative hair dye components, in order to achieve a desired color.

Hair Dye Constituents

The present invention incorporates one or more direct dyes and, optionally, hair dye primary intermediates and/or hair dye couplers within the reaction medium, with a view towards modifying the ultimate color effect produced on the hair. Thus, it is believed that these conventional hair dye components react with the various species formed during the reaction, thereby incorporating one or more additional chromophoric substituent groups within the ultimate melanin species. The presence of the chromophoric groups provides tonality modification so that a broad array of colors is available to the user. Because the reaction with the hair dye primary intermediates and/or couplers may prevent cyclization, nitrogenous phenolic melanin precursors are likely obtained in lieu of indolic melanin precursors.

The concentration of the direct dyes, couplers and/or primary intermediates is less than about 10 mg/ml, and preferably is present in the reaction medium from about 0.01 to about 5 mg/ml, most preferably from about 0.05 to about 2 mg/ml. The amount of these hair dye components should not be so great as to prevent the formation of indolic melanins, nor should it exceed the concentration of the dopa species. That is, the process of the present invention contemplates reaction of only a portion of the intervening dopa species reaction products with the direct dye or, if present, the primary intermediate and/or coupler compounds. Among these latter compounds, couplers are preferred as they are less likely to be oxidized by the ferricyanide oxidant. Because the ferricyanide will compete for reaction with the primary intermediates, adjustment in ferricyanide concentration and/or primary intermediate concentration might be required.

A wide variety of primary intermediates can be employed in this invention including, for example:

paraphenylenediamines, corresponding to the formula:

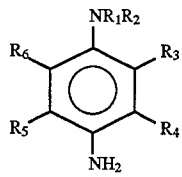

in which $R_1$ and $R_2$, which may be identical or different, can denote hydrogen, a $C_1$-$C_6$ lower alkyl group, a $C_1$-$C_6$ alkyl radical substituted with one or more hydroxy group(s) or with a methoxy, methylsulphonylamino or aminocarbonyl group, a furfuryl group, or a phenyl radical optionally substituted with an amino group; $R_3$ and $R_6$ denote, independently of one another, hydrogen, a $C_1$-$C_6$ lower alkoxy group, a halogen atom such as a chlorine atom, with one or more hydroxy group(s), and $R_4$ and $R_5$ denote, independently of one another, hydrogen, a $C_1$-$C_6$ lower alkoxy group, a $C_1$-$C_6$ lower alkyl group, or a halogen atom such as chlorine, as well as their salts with inorganic or organic acids. N,N'-diphenylalkylenediamines in which the phenyl groups are substituted at the para position with an OH or amino group optionally substituted with a $C_1$-$C_6$ alkyl group, to be substituted with $C_1$-$C_6$ alkyl, $C_1$-$C_6$ hydroxyalkyl or $C_1$-$C_6$ aminoalkyl; para-aminophenols; ortho-aminophenols; ortho-phenylenediamines, and heterocyclic oxidation bases.

Among the useful compounds of formula (I), there may be mentioned p-phenylenediamine, 2-methyl-paraphenylenediamine, 2-methoxy-para-phenylenediamine, 2-chloro-N-methyl-paraphenylenediamine, N-furfuryl-paraphenylenediamine, 3-methoxy-$N^1$-methyl-paraphenylenediamine, 2-chloro-para-phenylenediamine, N-methyl-para-phenylenediamine, 2,3-dimethyl-para-phenylenediamine, 5-chloro-$N^1$-methyl-p-phenylenediamine, 5-methyl-$N^1$,$N^1$-dimethyl-p-phenylenediamine, 5-methyl-$N^1$-ethyl-$N^1$-(amino-carbonyl-methyl)-p-phenylenediamine, 5-methyl-$N^1$-ethyl-$N^1$-ethylsulphonylamino-ethyl)-p-phenylenediamine, N-(2-methoxyethyl)-p-phenylenediamine, 2,6-dimethyl-p-phenylenediamine, N,N-bis(2-hydroxyethyl)-p-phenylenediamine. The N,$N^1$-diphenylalkylenediamines include, for example, N,$N^1$-bis-(2-hydroxyethyl)-N,$N^1$-bis (p-aminophenyl)-ethylenediamine. Their salts with acids such as the monohydrochlorides dihydrochlorides or sulphates are also suitable.

Among p-aminophenols which are more especially usable according to the invention, there may be mentioned p-aminophenol, 2-methyl-p-aminophenol, 3-methyl-p-aminophenol, 2,3-dimethyl-p-aminophenol, 3-methoxy-p-aminophenol, 2-chloro-p-aminophenol, N-methyl-p-aminophenol and 3-(methylthio)-p-aminophenol, of which p-aminophenol is preferred.

Among ortho bases, ortho-aminophenol, 5-chloro-orthoaminophenol and ortho-phenylenediamine are chosen more especially according to the invention.

Among heterocyclic bases, it is preferable, according to the invention, to use, 2,3-diamino-6-methoxy-pyridine and 2-(2-hydroxyethyl)amino-5-aminopyridine and their salts, and still more especially 3,6-diaminopyridine, 2,6-dimethoxy-3-amino-pyridine, 2-methylamino-3-amino-6-methoxypyridine, 2,5-diamino-pyridine, 2-(N-hydroxyethyl)amino-5-amino pyridine, and 2-(N,N-bishydroxyethyl)amino-5-aminopyridine.

More especially preferred primary intermediates are p-phenylenediamine 2-methyl-p-phenylenediamine, N-(2-methoxyethyl)-p-phenylenediamine, N,N-bis(2-hydroxyethyl)-p-phenylenediamine and p-aminophenol.

Among couplers or color modifiers there may be mentioned, in particular, the compounds corresponding to the formula:

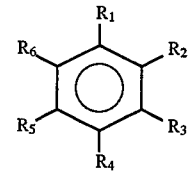

in which $R_1$ denotes hydroxy or an amino group which can be substituted with one or more $C_1$-$C_6$ hydroxyalkyl groups; $R_3$ and $R_5$, independently of one another, can denote hydrogen, a hydroxy group, an amino group optionally substituted with a $C_1$-$C_6$ lower hydroxyalkyl group or a $C_1$-$C_6$ lower alkyl group; and $R_2$, $R_4$ and $R_6$ can denote a hydrogen atom or a $C_1$-$C_6$ alkoxy group, a hydroxyalkoxy group or a $C_1$-$C_6$ lower alkyl group; it also being possible for $R_3$ and $R_4$ together to form a methylenedioxy group.

Among the suitable couplers, there may be mentioned 2-methoxy-5-aminophenol, 2-methoxy-5-[N-(2-hydroxyethyl)-amino]phenyl, 1,3-diamino-2,6-dimethoxybenzene, 2-methoxy-1-(N-methylamino)-4-(2-hydroxyethoxy)-3-amino-benzene, 1,3-diamino-6-methoxybenzene, 4,6-dimethoxy-1,3-bis[N-(2-hydroxyethyl)-amino]benzene, 2,6-dimethoxy-3-[N-(2-hydroxyethyl)amino]-1-aminobenzene, 2,6-dimethoxy-3-[N-(2-hydroxyethyl)amino]-1-aminobenzene, 2,4-dimethyoxy-3-[N-(2-hydroxyethyl)amino]phenol, 1,3-bis[N-(2-hydroxyethyl)amino]-4-methoxybenzene, 3-amino-4-methoxyphenol, 3,4-methylenedioxy-1-aminobenzene, 2,6-dimethyl-3-[N-(2-hydroxyethyl)amino]phenol, 2,6-dimethyl-3-aminophenol, 4-ethoxy-1-amino-3-[N,N-bis(2-hydroxyethyl)amino]benzene, (2,4-diaminophenoxy) ethanol, (2-amino-N-methyl-4-aminophenoxy)-ethanol, 1-methoxy-2-[N-(2-hydroxyethyl)amino]-4-aminobenzene, 3,4-methylenedioxy-6-methoxyphenol, 3-amino-6-methylphenol, 3,4-methylenedioxy-6-methoxyaminobenzene, 3-aminophenol, 1,3-dihydroxybenzene-4-(hydroxyethoxy)-1-,3-phenylenediamine, 4,6-(dihydroxyethoxy)-1-,3-phenylenediamine, and 1,3-phenylenediamine.

Other suitable couplers are 6-aminobenzomorpholine, 1-amino-7-naphthol, 6-hydroxybenzomorpholine, 1-naphthol, 1,3-dihydroxynaphthalene and 1,2-dihydroxybenzene. Among heterocyclic couplers there may be mentioned 2,6-dihydroxypyridine, 2,6-diaminopyridine, 2-amino-4-hydroxypyridine, 2-hydroxy-4-amino-pyridine, 2-hydroxy-5-aminopyridine, 2-amino-6-hydroxypyridine and the like. Included also are further derivatives of 2,6-diamino alkyl pyridines where the amino nitrogen of one or both amino groups is mono- or distributed with a $C_1$-$C_6$ alkyl group such as the methyl, propyl, isopropyl, butyl, iso or sec-butyl, pentyl, sec-pentyl neopoentyl, t-butyl, hexyl, 3-methyl pentyl or 4-methylpentyl groups. The amino groups of either the amino-4-hydroxy- or 2-hydroxy-4-amino-pyridines may also have mono- or di-$C_1$-$C_6$ alkylation on the nitrogen atoms.

The 2,6 amino-, or 4-amino-2-hydroxy- or 2-amino-4-hydroxy pyridine nitrogens may also either singly or doubly be derivatized with alkoxy substituents of carbon lengths of 1 to 6 with specific mention of 2-hydroxyethyl, 3-hydroxypropyl, 4-hydroxybutyl, 5-hydroxypentyl, 6-hydroxyhexl, 2-hydroxypropyl, 2-hydroxybutyl, 2-hydroxypentyl, 2-hydroxyhexyl, 3-hydroxybutyl, 3-hydroxypentyl, 2-hydroxyhexyl, 4-hydroxypentyl and 5-hydroxypentyl groups.

Among trihydroxylated derivatives of benzene, there may be mentioned 1,2,4-trihydroxybenzene, 1,2,4-trihydroxy-5-alkylbenzenes in which the alkyl group is a $C_1$-$C_6$ lower alkyl group and 1,2,3-trihydroxybenzene, and their salts.

Among diaminohydroxybenzenes, there may be mentioned 2,4-diaminophenol and 2,5-diamino-4-methoxy-1-hydroxybenzene, and their salts.

Among aminodihydroxybenzenes, there may be mentioned 2-amino-1,4-dihydroxybenzene, 1,4-dihydroxy-2-diethylaminobenzene and 4-aminoresorcinol, and their salts.

Among substituted 1,2-dihydroxybenzenes, 4-methyl-1,2-dihydroxybenzene and 3-methoxy-1,2-dihydroxybenzene are especially preferred.

The aminohydroxybenzenes are chosen, in particular, from 2-amino-4-methoxyphenol, 2-aminophenol, 4,6-dimethoxy-3-amino-1-hydroxybenzene and 2,6-dimethyl-4-[N-(p-hydroxy-phenyl)amino]-1-hydroxybenzene, and their salts.

By way of a triaminobenzene, there may be mentioned 1,5-diamino-2-methyl-4-[N-(p-hyroxyphenyl)amino]-benzene and its salts.

Also suitable as a coupler is N-acetyl dopa.

The table below lists some of the preferred primary intermediates and couplers for use in this invention.

| Preferred Primary Intermediates and Couplers | |
|---|---|
| Primary Intermediates: | p-phenylenediamine |
| | p-aminophenol |
| | o-aminophenol |
| | N,N-bis(2-hydroxyethyl)-p-phenylenediamine |
| | 2,5-diaminopyridine |
| | p-toluenediamine |
| Couplers: | resorcinol |
| | m-aminophenol |
| | 1-naphthol |
| | 5-amino-o-cresol |
| | 2-methylresorcinol |
| | N-acetyl dopa |
| | 4,6-di(hydroxyethoxy)-m-phenylenediamine |
| | m-phenylenediamine |

Direct dyes which can be employed in this invention alone or in combination with primary intermediates and/or couplers are colored aromatic nitroamines which as conventionally employed, deposit on the hair and impart a color which is not permanent, i.e. the color is washed out with ordinary shampoos after repeated shampooing. It has now been discovered that certain direct dyes will react with dopaquinone under the reaction conditions of this invention to form covalently bonded compounds which will impart a permanent color to the hair. Such substituted products will effect "permanent" changes in hair color as that term is defined in this disclosure. Such direct dyes will be referred to herein for convenience as "reactive direct dyes".

Reactive direct dyes are colored primary and secondary aromatic amines substituted with at least one nitro group in which the amino group is sufficiently nucleophilic so that the reactive direct dyes will react with dopaquinone with the formation of a covalent bond. The reactive direct dyes for use in this invention require at least one nitro group for color and at least one nucleophilic amino group for covalent bonding, but there may also be other substituents on the aromatic nucleus. These may be either electronegative or electropositive, the proviso being that such substituents do not so reduce the nucleophilicity of the amino group or otherwise interfere with the amino group, e.g. sterically, so as to render the formation of a covalent bond impossible.

It will be readily apparent to the skilled artisan that there is a large number of reactive direct dyes which will be useful in this invention. Those that are preferred may be represented by the formula:

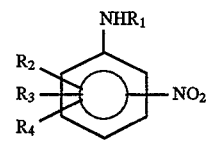

$R_1$ is H, lower alkyl ($C_1$-$C_6$), hydroxyalkyl ($C_1$-$C_6$) or phenyl, preferably H; $R_2$, $R_3$, $R_4$ which may be the same or different are electron donor or acceptor substitutents selected from the group consisting of H, lower alkyl ($C_1$-$C_6$), OH, OR, COOR, NHCOR in which R is lower alkyl ($C_1$-$C_6$) or hydroxyalkyl ($C_1$-$C_6$), CN, COOH, Hal, $NO_2$, $CF_3$, $SO_3H$ and $NR_5R_6$, in which $R_5$ and $R_6$ may be the same or different and are selected from the group consisting of H, lower alkyl ($C_1$-$C_6$), and substituted lower alkyl ($C_1$-$C_6$), in which the substituent may be OH, OR, $NHCOR_7$, $NHSO_2R_7$, $NHCONH_2$, $NHCO_2R_7$, $NHCSNH_2$, CN, COOH, $SO_3H$, $SO_2NR_7$, $SO_2R_7$, or $COOR_7$ in which $R_7$ is lower alkyl ($C_1$-$C_6$), lower hydroxyalkyl ($C_1$-$C_6$) or phenyl linked to the nitrogen by an alkylene chain, phenyl or substituted phenyl, with substituents defined as $R_2$ with the proviso that only one of $R_2$, $R_3$ or $R_4$ can be CN, COOH, Hal, $NO_2$, $CF_3$, $SO_3H$.

Other suitable, although less preferred reactive direct dyes include heterocyclic and fused ring analogs of the above described compounds such as analogs with pyridyl, quinolyl, isoquinolyl, benzofuranyl, isobenzofuranyl, thionaphthyl, isothionaphthyl, indolyl, isoindolyl or naphthyl nuclei.

The presently preferred compounds are
2-Nitro-p-phenylene diamine
4-amino-3-nitrophenol
2-amino-5-nitrophenol
4-N-hydroxyethylamino-3-nitro aniline
2-N-hydroxyethylamino-5-nitro-aniline Optional Adjuvant Constituents The variously described embodiments of the present invention may also include in the hair dye composition one or more optional ingredients, which may be provided in one or more additional containers of the kit for admixture by the user into the aqueous reaction mixture, or, if compatible, may be incorporated into the oxidant or dopa premix solutions described previously.

Well-known conventional additives usually employed in oxidative hair coloring compositions such as organic solvents, thickeners, surface-active agents, pH adjusting agents, antioxidants, fragrances and chelating agents may be included in the compositions of the inventions.

The hair dye compositions used in the process of the present invention can include an organic solvent as a cosolvent. The organic solvent may assist in the dissolution of the components of the composition, and is present typically in an amount up to about 30%, preferably up to about 15%. A desirable range is from about 0.1 to about 15%, most preferably from about 1 to 10%. Suitable solvents are mono- and polyhydric alcohols, for example, ethyl alcohol, isopropyl alcohol, propylene glycol, benzyl alcohol, etc., and glycol ethers, such as 2-butoxyethanol, ethylene glycol monoethyl ether and diethyleneglycol monoethyl ether.

Surface-active agents employed in the dyeing compositions of this invention can be anionic, nonionic, cationic, amphoteric or zwitterionic. By way of examples of the various types of surface-active agents, there can be mentioned: higher alkyl-benzene sulfonates; alkylnaphthalene-sulfonates; sulfonated esters of alcohols and polybasic acids; taurates; fatty alcohol sulfates; sulfates of branched chain or secondary alcohols; alkyldimethylbenzylammonium chlorides, salts of fatty acids or fatty acid mixtures; N-oxyalkylated fatty acid alkanolamides, and the like. Illustrative of specific surfactants there can be mentioned: sodium lauryl sulfate; polyoxyethylene lauryl ester, myristyl sulfate; glyceryl monostearate; triethanolamine oleate, sodium salt of palmitic methyl taurine; cetyl pyridinium chloride; lauryl sulfonate; myristyl sulfonate, lauric diethanolamide; polyoxyethylene stearate; ethoxylated oleoyl diethanolamide; polyethylene glycol amides of hydrogenated tallow; stearyldimethyl benzyl ammonium chloride; dodecylbenzene sodium sulfonate; triethanolamine salt of p-dodecylbenzene sulfonate; nonylaphthalene sodium sulfonate; dioctyl sodium sulfonsuccinate; sodium N-methyl-N-oleoyl taurate; oleic acid ester of sodium isothionate; sodium dodecyl sulfate; the sodium salt of 3-diethyl tridecanol-6-sulfate and the like. The quantity of surface-active agent can vary over a wide range, such as from about 0.05% to 15% and preferably from about 0.10 to 5% by weight of the composition. The anionic and nonionic surfactants are employed typically as emulsifiers, while the cationic surfactants are useful to impart a hair conditioning benefit to the hair. Care must be exercised when anionic and cationic surfactants are both incorporated, in view of possible incompatibility.

Chelating and sequestering agents include, for example, ethylenediaminetetraacetic acid, sodium citrate, etc., and are present in an amount of under about 1%.

A thickening agent may also be incorporated in the dyeing composition of this invention, which may be one or several of those commonly used in hair dyeing. These are exemplified by such products as sodium alginate or gum arabic, or cellulose derivatives, such as methylcellulose, e.g., Methocel 60HG, or the sodium salt of carboxymethylcellulose, or hydroxyethyl-cellulose, e.g., Cellosize QP-40 or acrylic polymers, such as polyacrylic acid sodium salt, or inorganic thickeners, such as bentonite. The quantity of this thickening agent can also vary over a wide range, even as high as 20%. Ordinarily it will range from about 0.1 to 5% by weight of the composition. The viscosity of the composition may vary from about 1 cp to about 100,00 cps. For a typical lotion formulation, composition viscosity is between about 100 cps to about 10,000 cps, at which viscosity the composition can be applied to the hair without running or dripping.

The composition of the present invention may also include pH adjustment agents to provide an initial reaction medium pH within the previously stated range. Typically, these pH adjustment agents are incorporated into dopa species premix, as previously described, to ensure dissolution of the dopa species. However, such pH adjustment agents may also be incorporated into the oxidant premix or directly into the aqueous reaction medium. Typical pH adjustment agents have been described in the section entitled The Dopa Species.

In alkaline solution the dopa salt may be somewhat susceptible to oxidation, for example, by air. Accordingly, a small amount of an antioxidant may be included in the alkaline dopa premix. In such instances the amount of oxidant in the oxidant premix might be increased to neutralize the remaining antioxidant upon admixture of the dopa species and the oxidant premixes.

This list of optional ingredients is not intended as limiting. Other suitable adjuvants for inclusion in the hair dye composition are recited, for example, in Zviak, *The Science of Hair Care* (1986) and Balsam and Sagarin, *Cosmetics: Science and Technology*, Vol. 2 (Second Edition 1972).

The invention is now illustrated by the following examples. Unless otherwise indicated, concentrations and ratios in the specification including the examples are on a weight basis by weight of the total composition.

EXAMPLES 1–9

15 ml of a 0.1M solution of dopa (pH about 1.9) was prepared by dissolving dopa in 0.1M hydrochloric acid. Also prepared was a 0.36M solution of potassium ferricyanide also containing a buffer. To form the aqueous reaction medium, equal volumes of the dopa and the oxidant-buffer premixes were combined in a vessel that was open to the atmosphere. The buffer and its concentration in the aqueous reaction medium is indicated in Table I. Initial pH values of the reaction medium were measured as noted in Table I. The 5,6-dihydroxyindole concentration was measured at 15 minutes following mixing of the premixes, as set forth in Table I, using HPLC techniques known in the art.

TABLE I

| Example | Buffer | Buffer Conc. | pH (immediately after mixing) | DHI Conc. at t = 15 min. (mg/ml) |
|---|---|---|---|---|
| 1 | Potassium phosphate | 0.36 M | 6.7 | 4.3 |
| 2 | Potassium phosphate | 0.59 M | 6.8 | 4.5 |
| 3 | Sodium bicarbonate | 0.70 M | 7.0 | 4.6 |
| 4 | Sodium borate | 0.50 M | 7.1 | 1.6 |
| 5 | HEPES | 0.33 M | 7.0 | 3.2 |
| 6 | ACES | 0.33 M | 7.1 | 3.4 |
| 7 | TRIZMA | 0.33 M | 7.5 | 4.8 |
| 8 | TAPS | 0.23 M | 7.7 | 3.4 |
| 9 | TAPS | 0.33 M | 7.6 | 4.1 |

The data in Table I shows that Examples 1–3 and 5–9 each produced after 15 minutes a DHI concentration well above the minimum peak concentration of 1.5 mg/ml required for a DHI-containing hair dye composition. Example 4, in which sodium borate was used as the buffer, achieved a 1.6 mg/ml DHI level after 15 minutes at the 0.50M buffer concentration (based on the oxidant premix) employed. Examples 1, 2, 8 and 9 indicate that DHI concentration is a function of buffer concentration. The levels of buffer employed in each of these examples were well above the buffer concentration needed to maintain reaction mixture pH in the range of 6 to 10.

EXAMPLE 10

0.15 g dopa was dissolved in 7.5 ml 0.1M hydrochloric acid to form the dopa premix. An oxidant premix containing 0.9 g potassium ferricyanide, 0.75 g sodium bicarbonate and 7.5 ml water was prepared and rapidly mixed with the dopa premix to form the aqueous reaction medium. The pH of the aqueous reaction medium immediately after mixing was 6.9. DHI concentrations were determined by HPLC analysis on aliquots of the reaction medium after 5 and 25 minutes. After 5 minutes the DHI concentration as 1.75 mg/ml, and after 25 minutes the DHI concentration was 6.4 mg/ml.

EXAMPLE 11

The ability of an aqueous composition containing dopa and a periodate to form DHI based on the teachings of U.S. Pat. No. 4,746,322 to Herlihy was investigated.

A dopa premix comprising 0.15 g dopa, 0.3 g benzyl alcohol and 10 ml water was prepared by admixture of these ingredients in an open breaker with stirring for about five minutes. 60 mg sodium periodate was then added, with adjustment of the pH to 5.0 with the addition of dilute hydrochloric acid. Aliquots of the solution were removed after 5, 25 and 45 minutes and tested for DHI presence using HPLC techniques. None of the aliquots contained a registrable level of DHI (i.e., less than 0.1 mg/ml DHI).

The experiment was repeated using 60 mg sodium iodate as the oxidant. Again, HPLC analysis failed to show registrable levels of DHI after 5, 25 and 45 minutes.

EXAMPLE 12

This Example illustrates the dyeing of hair in accordance with the process of the present invention using a reaction medium containing potassium ferricyanide as the oxidant and sodium phosphate as the buffer.

A dopa premix was prepared by adding 0.15 g dopa to 7.5 ml 0.1M hydrochloric acid. An oxidant premix comprising 0.9 potassium ferricyanide, 1.45 g sodium phosphate (1.15 g $Na_2HPO_4$ and 0.3 g $Na_3PO_4$ $12H_2O$) and 7.5 ml water was prepared, and rapidly admixed with the dopa premix to provide the aqueous reaction medium, which had an initial pH of 7.2.

A swatch of virgin gray hair was contacted with the aqueous reaction medium for 30 minutes, rinsed with water, shampooed and dried.

The color profile of the virgin and treated hair was evaluated using the Hunter Tristimulus method, which method is well known in the art. In the Hunter method, the parameters a and b may be positive or negative and define the chromatic condition of the hair. Thus, the more positive the a value, the greater the greenness of the hair. Similarly, positive b values indicate yellowness, while negative b values indicate blueness. More importantly, the L parameter is a measure of color intensity, and has a value of 0 for absolute black to 100 for absolute white. Generally, hair having an L value of about 15 or less is considered black, while an L value of about 60 is white. It should be understood that the L value scale is not linear, but rather is sigmoidal. Proximate to 0 and proximate to 100 hair color intensity apparent to the human eye varies minimally with unit changes in the L value. Between L values of about 20 to about 50, hair color intensity varies significantly with unit changes in L value. Thus, the Hunter values are more sensitive in the region where the human eye is able to perceive color changes.

The before and after Hunter values are as follows:

|  | L | a | b |
|---|---|---|---|
| Before dyeing (Virgin Hair) | 38.0 | −0.4 | 7.7 |
| After dyeing | 30.4 | 0.3 | 5.3 |

It is seen that the virgin gray hair was made several shades darker when treated in accordance with the process of the present invention.

EXAMPLE 13

The process of Example 12 was repeated, except that the swatch of virgin gray hair (L=38.0, a=−0.4, b=7.7) was first pretreated for 5 minutes with an alkaline shampoo containing conventional anionic surfactants and further containing 0.08M copper sulfate, rinsed thoroughly, and contacted for 30 minutes with the aqueous reaction medium described above. The hair was dyed black (L=16.5, a=0.6, b=1.3).

EXAMPLE 14

This Example illustrates the dyeing of hair in accordance with the process of the present invention using a reaction medium containing potassium ferricyanide as the oxidant and sodium bicarbonate as the buffer.

A dopa premix was formed by adding 0.15 g dopa to 7.5 ml 0.1M HCl. The oxidant premix contained 0.9 g potassium ferricyanide, 0.87 g sodium bicarbonate and 7.5 ml water, and was admixed rapidly with the dopa premix. The initial pH of the thus formed aqueous reaction medium was 7.1.

Virgin gray hair (as in Example 12) was contacted for 30 minutes, rinsed, shampooed and dried. The Hunter values for the hair dyed in this manner were L=25.6, a=0.5 and b=3.7.

EXAMPLE 15

The process of Example 14 was repeated but with a virgin gray hair swatch that was first treated for 5 minutes with the copper-containing shampoo described in Example 14. The swatch was dyed black (L=14.2, a=0.3 and b=0.6).

EXAMPLE 16

The process of Example 13 was repeated, except that the aqueous reaction medium was in contact with the swatch for only 10 minutes. The hair was dyed black (L=15.6, a=0.6 and b=1.1).

EXAMPLE 17

The process of Example 13 was repeated except the oxidant premix contained 1.4 g sodium phosphate as the buffer, and further contained 1.79 g sodium citrate to adjust the pH. The initial reaction medium pH was 9.6 and the contact time of the reaction medium with hair was 15 minutes. The hair was dyed black (L=13.7, a=0.4 and b=0.2).

EXAMPLE 18

The process of Example 13 was repeated except that the buffer was 0.6 g tris(hydroxymethyl)aminomethane. The initial pH was 7.5. The hair was dyed black (L=13.0, a=0.3 and b=0.3).

EXAMPLE 19

A dopa premix was made by adding 0.15 g dopa to 7.5 ml 0.1M HCl. The oxidant premix contained 0.15 g potassium permanganate, 1.1 g sodium phosphate (0.8 g $Na_2HPO_4$ and 0.3 g $NaH_2PO_4.H_2O$) and 7.5 ml water. Initial reaction medium pH was 7.3.

A swatch of virgin gray hair (L=37.9, a=−0.2 and b=8.5) was dyed by contacting the swatch with the aqueous reaction medium for 30 minutes. The swatch was several shades darker in color (L=33.8, a=−0.2 and b=6.7).

EXAMPLE 20

The process of Example 19 was repeated, but with a five-minute pretreatment with the copper shampoo. The hair was dark brown (L=21.8, a=−0.2 and b=2.1).

EXAMPLES 21-22

Hair was dyed in accordance with the present invention as described below.

Hair dye compositions were prepared by mixing a first solution containing 0.15 g dopa, 0.08 g m-aminophenol and 7.5 ml 0.1M HCl, and a second solution containing potassium ferricyanide in an amount as set forth in Table II, 7.5 ml water and phosphate buffer (1.15 g $Na_2HPO_4$; 0.3 g $Na_3PO_4.12H_2O$) to provide an initial pH of the hair dye composition as stated in Table II, i.e., as measured after mixing of the first and second solutions. Hair tresses having Hunter Tristimulus Values of L=34.5, 1=0.1 and b=7.0 were dyed by applying each of the compositions to a tress for 30 minutes. The tresses were then rinsed, shampooed with a conventional shampoo and dried. The final Hunter values of the dyed tresses are reported in Table II.

TABLE II

| No. | Oxidant (g) | Initial pH | Hunter Tristimulus Value | | | Color |
|---|---|---|---|---|---|---|
| | | | L | a | b | |
| 21 | 0.9 | 7.1 | 30.0 | 0.5 | 7.0 | Gray yellow |
| 22 | 0.5 | 7.5 | 27.4 | 0.8 | 6.7 | Ash brown |

EXAMPLES 23-24

Hair per Examples 21-22 above was similarly dyed, but with the application of a copper-containing shampoo to the hair as a pre-treatment. The shampoo contained 1% copper sulfate. The results are set forth below in Table III.

TABLE III

| No. | Oxidant (g) | Initial pH | Hunter Tristimulus Value | | | Color |
|---|---|---|---|---|---|---|
| | | | L | a | b | |
| 23 | 0.9 | 7.1 | 21.5 | 1.4 | 4.6 | Dark brown |
| 24 | 0.5 | 7.5 | 21.2 | 1.7 | 4.9 | Dark brown |

EXAMPLES 25-27

Gray hair was dyed using a mixture of dopa and an amount of m-aminophenol (m-AP) identified in Table IV below. The hair dye composition contained 0.9 g potassium ferricyanide. Conditions were otherwise the same as in Examples 21-22. The gray hair to be dyed had initial Hunter values of L=36.0, a=0.2 and b=7.6.

TABLE IV

| No. | m-AP (g) | Initial pH | Hunter Tristimulus Value | | | Color |
|---|---|---|---|---|---|---|
| | | | L | a | b | |
| 25 | 0.08 | 7.1 | 30.0 | 0.5 | 7.0 | Gray yellow |
| 26 | 0.05 | 7.1 | 29.9 | 0.4 | 7.0 | Light brown yellow |
| 27 | 0.02 | 7.1 | 28.4 | 0.3 | 5.3 | Light ash brown |

EXAMPLES 28-30

Gray hair described in Examples 25-27 was dyed as in Examples 25-27, but with the application of a copper-containing shampoo as a pretreatment per Examples 23-24. The results were as follows.

TABLE V

| No. | m-AP (g) | Initial pH | Hunter Tristimulus Value | | | Color |
|---|---|---|---|---|---|---|
| | | | L | a | b | |
| 28 | 0.08 | 7.1 | 21.5 | 1.4 | 4.6 | Dark brown |
| 29 | 0.05 | 7.1 | 21.9 | 1.1 | 5.1 | Dark brown |
| 30 | 0.02 | 7.1 | 15.7 | 0.3 | 0.9 | Black gray |

EXAMPLES 31-35

A hair dye composition was provided by mixing a first solution containing 0.15 g dopa, 0.15 g of a hair dye component identified in Table VI below and 7.5 ml 0.1 MHCl, and a second solution containing 0.9 g potassium ferricyanide, sufficient phosphate buffer to provide an initial pH of about 7 and 7.5 ml water. Hair tresses having a Hunter value of L=35.0, a=0.2 and b=7.3 were dyed by first pretreating the tress with a copper sulfate-containing shampoo, and thereafter applying a composition of Table VI to a tress for 30 minutes. The tresses were then rinsed, shampooed with a conventional shampoo and dried. Thereafter, Hunter Tristimulus readings were obtained for each tress as reported below.

TABLE VI

| No. | Coupler | Hunter Tristimulus Value | | | Color |
|---|---|---|---|---|---|
| | | L | a | b | |
| 31 | Resorcinol | 17.3 | 0.6 | 2.5 | Brown black |
| 32 | 2,6-Dihydroxypyridine | 25.9 | 1.4 | 3.6 | Gray violet |
| 33 | 2,6-Diaminopyridine | 23.4 | 0.3 | 2.5 | Dark gray |
| 34 | 3-Amino-6-(dimethyl-amino)-methylphenol | 21.4 | 0.6 | 4.2 | Brown |
| 35 | 1-Naphthol | 21.6 | −1.1 | 0.9 | Greenish gray |

EXAMPLES 36-38

Gray hair (L=34.0; a=0.2; b=6.9) was dyed with a composition containing 0.075 g dopa; 0.091 g N-acetyl dopa; 0.9 g ferricyanide; sufficient phosphate buffer to provide an initial composition pH of 7.2, and 15 ml water. In Example 36 there was no additional treatment of the hair. In Example 37 there was a copper pretreatment step as previously described, and in Example 38 the hair dye composition further contained 0.69% potassium iodide and treatment with the hair dye composition was followed by a post-treatment of a 3% $H_2O_2$ solution, pH adjusted to 9.5 with sodium carbonate.

TABLE VII

| No. | Other Treatment | Hunter Tristimulus Value | | | Color |
|---|---|---|---|---|---|
| | | L | a | b | |
| 36 | None | 30.2 | 0.3 | 5.2 | Gray |
| 37 | Cu Pretreatment | 23.6 | 1.2 | 2.9 | Dark brown |
| 38 | KI w/$H_2O_2$ Post-treatment | 32.0 | −0.3 | 8.6 | Yellow |

EXAMPLES 39-40

Blended gray hair was dyed with a hair dyeing composition containing 0.15 g dopa; 0.08 g m-AP; 0.15 g potassium permanganate and a buffer comprising 0.1 g $NaH_2PO_4$ and 0.1 g $Na_2HPO_4$, in 15 ml water, the composition having an initial pH of 6.8.

TABLE VIII

| No. | Other Treatment | Hunter Tristimulus Value | | | Color |
| | | L | a | b | |
| --- | --- | --- | --- | --- | --- |
| 39 | w/o Pretreatment | 30.4 | 0.8 | 7.0 | Light brown |
| 40 | w/Pretreatment w/copper shampoo | 20.6 | 1.0 | 4.2 | Dark brown |

EXAMPLES 41–43

Hair was dyed in accordance with the present invention as described below.

Hair dye compositions were prepared by mixing a first solution containing an amount of the dopa species identified in Table IX equal to 0.15 g dopa on an equimolar concentration basis and 7.5 ml 0.1M HCl, and a second solution containing 0.9 g potassium ferricyanide, 7.5 ml water and sufficient phosphate buffer to provide an initial pH of the hair dye composition of 7.2, i.e., after mixing of the first and second solutions. Hair tresses having Hunter Tristimulus Values of L=38.2, a=0.2 and b=7.8 were dyed by applying each of the compositions to a tress for 30 minutes. The tresses were then rinsed, shampooed with a conventional shampoo and dried. The final Hunter values of the dyed tresses are reported in Table IX.

TABLE IX

| No. | Dopa Species | Hunter Tristimulus Value | | | Color |
| | | L | a | b | |
| --- | --- | --- | --- | --- | --- |
| 41 | α-Methyl dopa | 32.7 | 0.8 | 4.9 | Light gray brown |
| 42 | Epinephrine | 32.8 | 0.8 | 10.4 | Gray yellow |
| 43 | Dopa methyl ester | 33.6 | 0.4 | 6.7 | Ash gray |

EXAMPLES 44–46

Hair per Examples 41–43 above was similarly dyed, but with the application of a copper-containing shampoo to the hair as a pre-treatment. The shampoo contained 1% copper sulfate. The results are set forth below in Table X.

TABLE X

| No. | Dopa Species | Hunter Tristimulus Value | | | Color |
| | | L | a | b | |
| --- | --- | --- | --- | --- | --- |
| 44 | α-Methyl dopa | 20.5 | 1.9 | 2.5 | Dark brown |
| 45 | Epinephrine | 22.4 | 1.8 | 6.1 | Brown yellow |
| 46 | Dopa methyl ester | 27.8 | 2.5 | 5.5 | Medium brown |

EXAMPLES 47–49

Gray hair was dyed using a mixture of the dopa species identified in Table XI below, the hair dye composition further containing 0.075 g dopa. The dopa species was present in an equimolar amount to dopa. Conditions were otherwise the same as in Examples 41–43. The gray hair to be dyed had initial Hunter values of L=34.0, a=0.2 and b=6.9.

TABLE XI

| No. | Dopa Species | Hunter Tristimulus Value | | | Color |
| | | L | a | b | |
| --- | --- | --- | --- | --- | --- |
| 47 | Epinephrine | 28.2 | −0.1 | 7.5 | Light ash brown |
| 48 | α-Methyl dopa | 28.1 | 0.5 | 4.0 | Gray brown |
| 49 | Dopa methyl ester | 31.4 | 0.4 | 5.4 | Gray |

EXAMPLES 50–52

Gray hair described in Examples 47–49 was dyed with a dopa species-dopa mixture as in Examples 47–49, but with the application of a copper-containing shampoo as a pre-treatment per Examples 4–6. The results were as follows.

TABLE XII

| No. | Dopa Species | Hunter Tristimulus Value | | | Color |
| | | L | a | b | |
| --- | --- | --- | --- | --- | --- |
| 50 | Epinephrine | 19.8 | −0.1 | 3.2 | Dark ash brown |
| 51 | α-Methyl dopa | 18.2 | 0.7 | 1.3 | Brown black |
| 52 | Dopa methyl ester | 19.0 | 0.5 | 1.5 | Black brown |

EXAMPLES 53–55

Gray hair swatches described in Examples 47–49 were treated with a dopa species-dopa mixture as in Examples 47–49, but with 0.69% potassium iodide present in the hair dyeing composition and followed by a hydrogen peroxide post-treatment. The post-treatment solution contained 3% $H_2O_2$ adjusted with sodium carbonate to pH 9.5.

The results are provided in Table XIII.

TABLE XIII

| No. | Dopa Species | Hunter Tristimulus Value | | | Color |
| | | L | a | b | |
| --- | --- | --- | --- | --- | --- |
| 53 | α-Methyl dopa | 18.7 | −0.5 | 1.5 | Brown black |
| 54 | Epinephrine | 17.1 | 0.0 | 1.4 | Gray black |
| 55 | Dopa methyl ester | 18.1 | 0.5 | 0.8 | Black brown |

EXAMPLES 56–57

A hair dye composition was provided by mixing a first solution contain an amount of a dopa species identified in Table XIV below equal to 0.15g dopa on an equimolar concentration basis, 0.25 g meta-amenophenol and 7.5 ml 0.1M HCl, and a second solution containing 0.9 g potassium ferricyanide, sufficient phosphate buffer to provide an initial pH of 7.2, and 7.5 ml water. Hair tresses having a Hunter value of L=38.2, 1=0.1 and b=7.8 were dyed by applying a composition to a tress for 30 minutes. The tresses were then rinsed, shampooed with a conventional shampoo and dried. Thereafter, Hunter Tristimulus readings were obtained for each tress as reported below.

TABLE XIV

| No. | Dopa Species | Hunter Tristimulus Value | | | Color |
|---|---|---|---|---|---|
| | | L | a | b | |
| 56 | α-Methyl dopa | 33.6 | −0.7 | 6.8 | Greenish gray |
| 57 | Epinephrine | 30.3 | 1.5 | 9.0 | Light brown yellow |

EXAMPLES 58–59

Examples 56–57 above were repeated but with application of a copper-containing shampoo as a pretreatment.

TABLE XV

| No. | Dopa Species | Hunter Tristimulus Value | | | Color |
|---|---|---|---|---|---|
| | | L | a | b | |
| 58 | α-Methyl dopa | 21.9 | 2.6 | 3.8 | Chestnut brown |
| 59 | Epinephrine | 21.7 | 3.4 | 5.4 | Red brown |

EXAMPLES 60–63

Same as Examples 56–59, except the hair dyeing composition contained 0.075 g dopa and an amount of the dopa species of Table XVi equal to 0.075 g dopa on an equimolar concentration basis. A copper pretreatment step was included only in Examples 62 and 63. The results are set forth in Table XVI.

TABLE XVI

| No. | Dopa Species | Hunter Tristimulus Value | | | Color |
|---|---|---|---|---|---|
| | | L | a | b | |
| 60 | α-Methyl dopa | 28.1 | 0.6 | 6.2 | Gray brown |
| 61 | Epinephrine | 28.2 | 0.6 | 6.6 | Light ash brown |
| 62 | α-Methyl dopa | 20.0 | 1.8 | 4.1 | Dark red brown |
| 63 | Epinephrine | 21.4 | 1.5 | 4.8 | Dark brown |

The following examples illustrate the dyeing of hair in accordance with the process of the present invention using a direct dye for a lasting color modification.

EXAMPLE 64

A hair dye composition was provided by mixing a first solution containing 0.2 g DOPA, 0.13 g $Na_2CO_3$, 0.5 g triethanolamine (TEA) and 0.18 g 2-nitro-p-phenylene diamine in 10 g total with a second solution containing 1.2 g potassium ferricyanide, 0.06 g $Na_2CO_3$ and 0.02 g citric acid in 10 g total solution. The pH after mixing was approx. 7–8. The composition was applied to (gray) hair, left for 20 minutes and rinsed off. Afterwards the swatch was exposed to an aqueous solution of $NaIO_4$ (5%) for 2 minutes, rinsed and dried. A reddish brown color was imparted to the hair.

| | Hunter Tristimulus values | | | |
|---|---|---|---|---|
| | L | a | b | |
| before dyeing | 39.0 | 0.25 | 6.75 | gray |
| after dyeing | 19.45 | 4.24 | 3.93 | reddish brown |

EXAMPLE 65

The colored swatch from Example 64 was exposed to 5 cycles of shampooing with a typical commercial shampoo. Hunter Tristimulus Values were measured after each cycle. The color remained essentially unchanged after 5 cycles of shampooing.

| | Hunter Tristimulus values | | | |
|---|---|---|---|---|
| | L | a | b | |
| before shampooing | 19.45 | 4.24 | 3.93 | reddish brown |
| after shampooing | 19.64 | 4.59 | 4.20 | reddish brown |

The following examples illustrate the dyeing of hair in accordance with the process of the present invention using a coupler and a direct dye simultaneously for a lasting color modification.

EXAMPLE 66

A hair dye composition was prepared by mixing a first solution containing 0.06 g DOPA, 0.064 g $Na_2CO_3$, 0.25 g triethanolamine (TEA) and 0.03 g 4-amino-3-nitrophenol in water to a total of 10 g with a second aqueous solution, containing 0.36 g potassium ferricyanide, 0.03 g $Na_2CO_3$ and 0.01 g citric acid in 10 g total solution. The pH after mixing was apprx. 8.3. The composition was applied to white hair (Piedmont), left for 5 minutes and removed by rinsing. Afterwards the swatch was exposed to an aqueous solution of $NaIO_4$ (1%) for 2 minutes, rinsed and dried. The hair was dyed to a blond shade.

| | Hunter Tristimulus Values | | |
|---|---|---|---|
| dyed hair: | L 45.5 | a 3.5 | b 13.9 |
| undyed hair: | L 67.5 | a −1.0 | b 18.0 |

The color remained essentially unchanged after several cycles of shampooing.

EXAMPLE 67

The dyeing composition of Example 66 was prepared and applied to white hair (Piedmont) and allowed to remain for 15 minutes. The dyeing mixture was rinsed off and the swatch was exposed to an aqueous solution of $NaIO_4$ (1%) for 2 minutes, rinsed and dried.

The hair was dyed to a light brown color.

| Hunter Tristimulus Values | | |
|---|---|---|
| L 33.7 | a 3.3 | b 10.8 |

The color remained essentially unchanged after several cycles of shampooing.

EXAMPLES 68–72

Hair dye compositions were prepared as described in Example 64 utilizing m-amino phenol (m-AP) as a coupler or p-amino phenol (p-AP) as a primary intermediate together with a direct dye of the structure and concentrations listed as Modifier 2 in Table XVII below. Hair was dyed as described in Table XVII. The results are set forth in Table XVII. The color of the swatches remained essentially unchanged after several cycles of shampooing.

TABLE XVII

Dyeing of bleached (bl) and gray (gr) hair with DOPA (1%), two modifiers and ferricyanide*

| No. | Modifier 1 [%] | Modifier 2 [%] | hair | Hunter Tris. Val. L | a | b |
|---|---|---|---|---|---|---|
| 68 | m-AP [0.2] | 2-Amino-5-nitro phenol [0.39] | bl | 19.0 | 5.2 | 9.0 |
|    |            |                               | gr | 22.1 | 2.5 | 10.5 |
| 69 | m-AP [0.2] | 4-Amino-3-nitro phenol [0.39] | bl | 18.6 | 5.7 | 7.4 |
|    |            |                               | gr | 18.8 | 4.3 | 7.2 |
| 70 | m-AP [0.2] | 5-Amino-2-methoxypyridine [0.31] | bl | 29.6 | 6.4 | 13.6 |
|    |            |                                  | gr | 27.1 | 2.6 | 9.4 |
| 71 | m-AP [0.2] | (2-N-hydroxyethyl Amino-5-nitro aniline | bl | 18.4 | 6.3 | 8.3 |
|    |            |                                         | gr | 22.5 | 2.9 | 10.2 |
| 72 | p-AP [0.25] | 2-nitro-p-phenylene diamine | bl | 20.2 | 8.1 | 8.2 |
|    |             |                             | gr | 21.3 | 4.8 | 6.4 |

*Dyeing time 15 minutes; oxidative post-treatment 1% $NaIO_4$, 2 minutes

What is claimed is:

1. A method of permanently dyeing hair with a melanin precursor comprising the steps of:
   (a) forming an aqueous reaction medium containing a dopa species selected from the group consisting of dopa, alpha alkyl dopa having 1 to 4 carbon atoms in the alkyl group, epinephrine and dopa alkyl esters having 1 to 6 carbon atoms in the alkyl group, a reactive direct dye that is a nitrobenzene direct dye substituted with at least one nucleophilic amino group and an oxidant selected from the group consisting of soluble ammonium, alkali metal or alkaline earth metal ferricyanide salts, each of the dopa species, reactive direct dye and oxidant being present in an amount effective to produce a reaction between the dopa species, the oxidant, and the reactive direct dye, and to produce a coloring concentration of a melanin precursor in the aqueous reaction medium, wherein a stoichiometric equivalent ratio of the dopa species to the ferricyanide oxidant is from about 0.95:1 to about 2:1, said aqueous reaction medium further containing a buffering agent in an amount sufficient to maintain the pH of aqueous reaction medium between about 6 to about 10,
   (b) contacting the hair with the aqueous reaction medium and allowing the melanin precursor to diffuse into the hair in an amount sufficient to generate a hair coloring amount of melanin, and
   (c) permanently coloring the hair by allowing the melanin precursors present in the hair to form melanin.

2. The method of claim 1 wherein the aqueous reaction medium additionally contains a hair dye primary intermediate, a hair dye coupler or a mixture thereof.

3. The method of claim 1 wherein the dopa species is dopa or an acid or basic salt thereof.

4. The method of claim 1 wherein the dopa species is an alkyl ester of dopa wherein the alkyl group contains 1 to 6 carbon atoms.

5. The method of claim 1 wherein the buffering agent is selected from the group consisting of ammonium, sodium and potassium salts of phosphates, carbonates, bicarbonates and borates and aminic buffers, and wherein the oxidant is sodium or potassium ferricyanide.

6. The method of claim 2 wherein the primary intermediate is selected from the group consisting of p-phenylenediamine, p-aminophenol, o-aminophenol N,N-bis(2-hydroxyethyl)-p-phenylenediamine, 2,5-diaminopyridine and p-toluenediamine and the coupler is selected from the group consisting of resorcinol, m-aminophenol, 1-naphthol, 5-amino-o-cresol, 2-methylresorcinol, N-acetyldopa, 4,6-di(hydroxyethoxy)-m-phenylenediamine and m-phenylenediamine.

7. The method of claim 1, 2, 3, 4, 5 or 6 wherein the reactive direct dye is selected from the group consisting of 2-nitro-p-phenylenediamine, 4-amino-3-nitrophenol, 4-N-hydroxy-ethylamino-3-nitroaniline and 2-N-hydroxy-ethylamino-5-nitroaniline.

8. A hair dyeing kit for permanently dyeing hair with melanin formed from a melanin precursor which includes in a single package a plurality of containers, the kit comprising (a) a first container containing a dopa species selected from the group consisting of dopa, alpha alkyl dopa having 1 to 4 carbon atoms in the alkyl group, epinephrine and dopa alkyl esters having 1 to 6 carbon atoms in the alkyl group and a reactive direct dye that is a nitrobenzene direct dye substituted with at least one nucleophilic amino group; (b) a second container containing as an oxidant component a water-soluble ammonium, alkali metal or alkaline earth metal ferricyanide salt, and in one of said containers or a separate container a buffering agent selected from the group consisting of aminic buffers and ammonium and alkali metal salts of phosphates, carbonates, bicarbonates and borates, the amount of buffering agent contained in the kit being sufficient to provide a pH of from about 6 to about 10 when the contents of the container are mixed, the dopa species and oxidant component in the kit being present in a stoichiometric equivalent ratio of from about 0.95:1 to about 2:1 dopa to oxidant, and wherein each of the dopa species, reactive direct dye and oxidant are present in amounts effective to produce a reaction between the dopa species, the oxidant, and the reactive direct dye.

9. The kit of claim 8 wherein the kit additionally contains a hair dye primary intermediate, a hair dye coupler or a mixture thereof in the first container or a separate container.

10. The kit of claim 8 wherein the dopa species is dopa or an acid or basic salt thereof.

11. The kit of claim 8 wherein the dopa species is an alkyl ester of dopa wherein the alkyl group contains 1 to 6 carbon atoms.

12. The kit of claim 8 wherein the buffering agent is selected from the group consisting of ammonium, sodium and potassium salts of phosphates, carbonates, bicarbonates, borates and aminic buffers, and wherein the oxidant is sodium or potassium ferricyanide.

13. The kit of claim 9 wherein the primary intermediate is selected from the group consisting of p-phenylenediamine, p-aminophenol, o-aminophenol N,N-bis(2-hydroxyethyl)-p-phenylenediamine, 2,5-diaminopyridine and p-toluenediamine and the coupler is selected from the group consisting of resorcinol, m-aminophenol, 1-naphthol, 5-amino-o-cresol, 2-methylresorcinol, N-acetyldopa, 4,6-di(hydroxyethyoxy)-m-phenylenediamine and m-phenylenediamine.

14. The kit of claim 8, 9, 10, 11, 12 or 13 wherein the reactive direct dye is selected from the group consisting of 2-nitro-p-phenylenediamine, 4-amino-3-nitrophenol, 4-N-hydroxy-ethylamino-3-nitroaniline and 2-N-hydroxy-ethylamino-5-nitroaniline.

15. The method of claim 1 further comprising the step of applying to the hair an effective amount of an agent to promote melanin formation.

16. The method of claim 15 wherein the agent is from about 0.001 to about 1% solution of metal salt selected from the group consisting of copper, zinc, nickel and iron salts and mixtures thereof.

17. The method of claim 15 wherein the agent is an iodide salt solution, said solution being applied to the hair in advance of treatment with a hydrogen peroxide solution.

18. The method of claim 16 wherein the metal salt is a copper II salt.

19. The method of claim 15 wherein the agent is an oxidizing solution applied to the hair as a post-treatment.

20. The hair dyeing kit of claim 8 wherein the kit further contains an agent to promote melanin formation.

21. The hair dyeing kit of claim 20 wherein the agent is a solution containing from about 0.001 to about 1% of a metal salt selected from the group consisting of copper, zinc, nickel and iron salts and mixtures thereof.

22. The hair dyeing kit of claim 20 wherein the agent is an iodide salt solution, said solution being applied to the hair in advance of treatment with a hydrogen peroxide solution.

23. The hair dyeing kit of claim 21 wherein the metal salt is a copper II salt.

24. The method of claim 1 wherein the reactive direct dye has the following chemical structure:

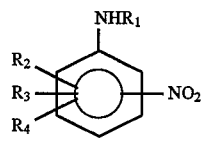

I wherein: $R_1$ is H, $C_1$ to $C_6$ alkyl, $C_1$ to $C_6$ hydroxyalkyl and phenyl; $R_2$, $R_3$ and $R_4$, which may be the same or different, are electron donor or acceptor substituents selected from the groups consisting of H, $C_1$ to $C_6$ alkyl, OH, OR, COR, NHCOR, CN, COOH, halogen, $NO_2$, $CF_3$, $SO_3H$, and $NR_5R_6$; R is $C_1$ to $C_6$ alkyl and $C_1$ to $C_6$ hydroxyalkyl; $R_5$ and $R_6$, which may be the same or different, are H, $C_1$ to $C_6$ alkyl and substituted $C_1$ to $C_6$ alkyls in which the substituent may be OH, OR, $NHCOR_7$, $NHSO_2R_7$, $NHCONH_2$, $NHCO_2R_7$, $NHCSNH_2$, CN, COOH, $SO_3H$, $SO_2NR_7$, $SO_2R_7$ and $COOR_7$, and $R_7$ is $C_1$ to $C_6$ alkyl, $C_1$ to $C_6$ hydroxyalkyl, phenyl linked to the nitrogen by an alkylene chain, phenyl and phenyl substituted with substituents defined as $R_2$, with the proviso that only one of $R_2$, $R_3$ or $R_4$ can be CN, COOH, halogen, $NO_2$, $CF_3$ and $SO_3H$.

25. The kit of claim 8 wherein the reactive direct dye has the following chemical structure:

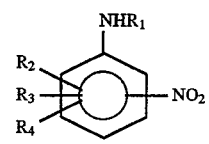

I wherein: $R_1$ is H, $C_1$ to $C_6$ alkyl, $C_1$ to $C_6$ hydroxyalkyl and phenyl; $R_2$, $R_3$ and $R_4$, which may be the same or different, are electron donor or acceptor substituents selected from the groups consisting of H, $C_1$ to $C_6$ alkyl, OH, OR, COOR, NHCOR, CN, COOH, halogen, $NO_2$, $CF_3$, $SO_3H$, and $NR_5R_6$; R is $C_1$ to $C_6$ alkyl and $C_1$ to $C_6$ hydroxyalkyl; $R_5$ and $R_6$, which may be the same or different, are H, $C_1$ to $C_6$ alkyl and substituted $C_1$ to $C_6$ alkyls in which the substituent may be OH, OR, $NHCOR_7$, $NHSO_2R_7$, $NHCONH_2$, $NHCO_2R_7$, $NHCSNH_2$, CN, COOH, $SO_3H$, $SO_2NR_7$, $SO_2R_7$ and $COOR_7$; $R_7$ is $C_1$ to $C_6$ alkyl, $C_1$ to $C_6$ hydroxyalkyl, phenyl linked to the nitrogen by an alkylene chain, phenyl and phenyl substituted with substituents defined as $R_2$, with the proviso that only one of $R_2$, $R_3$ or $R_4$ can be CN, COOH, halogen, $NO_2$, $CF_3$ and $SO_3H$.

* * * * *